United States Patent [19]
Kurth

[11] Patent Number: 5,981,212
[45] Date of Patent: Nov. 9, 1999

[54] WAY OF INCREASING THE RIBOFLAVIN CONTENT IN SPRAY-DRIED DISCHARGES FROM RIBOFLAVIN FERMENTATIONS

[75] Inventor: Roland Kurth, Limburgerhof, Germany

[73] Assignee: BASF Aktiengesellschaft, Ludwigshafen, Germany

[21] Appl. No.: 07/795,158

[22] Filed: Nov. 20, 1991

[30] Foreign Application Priority Data

Nov. 24, 1990 [DE] Germany .............................. 40 37 441

[51] Int. Cl.⁶ ..................................................... C12P 25/00
[52] U.S. Cl. ............................. 435/66; 435/267; 435/171
[58] Field of Search ................................ 435/66, 267, 171

[56] References Cited

U.S. PATENT DOCUMENTS 4,165,250   8/1979   Epstein et al. .

FOREIGN PATENT DOCUMENTS 211 289    of 0000   European Pat. Off. .
231 605    of 0000   European Pat. Off. .
29 20 592  of 0000   Germany .
34 20 310  of 0000   Germany .

OTHER PUBLICATIONS

Yamamura et al. Saccharomyces Yeast Cells grown at elevated temperatures are susceptible to antolysis. Agric Biol. Chem. 55(11):2861–2864 (1991).
Acta Biotechnol. 5 (1985) 2, 129–136.
Chem. Ing. Tech. 59 (1987) Nr. 2.S. 112–117.

Primary Examiner—Leon B. Lankford, Jr.
Attorney, Agent, or Firm—Keil & Weinkauf

[57] ABSTRACT

A process for increasing the riboflavin content in spray-dried discharges from riboflavin fermentations comprises inducing the lysis of the cells contained in the fermentation discharge by specific production or activation of enzymes which break down the cell walls and proteins. This autolysis can be induced in the riboflavin-producing strains of *Ashbya gossypii*, *Eremothecium ashbyii* and other microorganisms by incubation at from 35 to 55° C. with substantial exclusion of oxygen for from 6 to 28 hours.

3 Claims, No Drawings

WAY OF INCREASING THE RIBOFLAVIN CONTENT IN SPRAY-DRIED DISCHARGES FROM RIBOFLAVIN FERMENTATIONS

The present invention relates to increasing the riboflavin content in spray-dried discharges from riboflavin fermentations by specific autolysis of the cells contained in the fermentation solution.

The preparation of riboflavin (vitamin B2) by microbial fermentation processes is known. Thus, riboflavin can be obtained, for example, as disclosed in DE 29 20 592 by fermentation of *Ashbya gossypii* or *Eremothecium ashbyii*, as disclosed in EP 211 289 by fermentation of yeast belonging to Saccharomyces or a variant thereof, as disclosed in EP 231 605 using *Candida flareri* and as disclosed in DE 34 310 using *Bacillus subtilis*.

The solubility of riboflavin in aqueous solutions is about 70 to 200 mg per liter. Microorganisms which, under suitable conditions, produce more than 5 g of riboflavin per liter of fermentation solution in 5 days are described in the literature. Most of the riboflavin prepared in this way is thus present as crystals in the fermentation solution. The riboflavin prepared in this way is mainly employed for livestock nutrition and it is therefore sufficient in many cases to remove the crystalline riboflavin together with the biomass by decantation or centrifugation of the discharges from the fermenter, and to spray dry the resulting sediment. Products with riboflavin contents of about 20 to 60% by weight are obtained in this way. For other uses, especially for pharmaceutical purposes, riboflavin must be further purified.

Thus, DE-C 29 20 592 discloses a process for removing riboflavin from fermenter suspensions in which the latter are diluted with from 25 to 100% by volume of water and subsequently heated at from 50 to 65° C. for from 15 to 45 minutes in order to open up the cells containing the riboflavin. The suspension is cooled and then centrifuged twice to concentrate riboflavin. In order to increase the riboflavin content, it is recommended that a proteolytic enzyme is added to the diluted broth during the heating or, preferably, thereafter and allowed to act for from 3 to 4 hours. Examples given of suitable enzymes are alkaline proteases such as *B. subtilis* protease and *B. ligninoformis* protease or neutral proteases such as *B. subtilis* proteases. Enzymes of this type are commercially available. The disadvantage of the process disclosed in DE 29 20 592 is that the dilution results in a considerably larger volume of fermenter suspension to be worked up, which necessarily increases the costs thereof and the losses of riboflavin due to some of it dissolving in the added water. In addition, the proteolytic enzymes which are added are relatively costly.

It is an object of the present invention to develop a process with whose aid the riboflavin content in spray-dried discharges from riboflavin fermentations is increased in the most straightforward and economic manner possible, and the loss of riboflavin during working up is minimized.

We have found that this object is achieved by utilizing the specific autolysis of riboflavin-producing microorganisms to prepare a spray-dried product with a higher riboflavin content.

The present invention accordingly relates to a process for increasing the riboflavin content in spray-dried discharges from riboflavin fermentations, which comprises inducing the lysis of the cells contained in the fermentation solution, which contains the maximum yield of riboflavin, by specific production or activation of the enzymes which break down the intracellular cell wall and proteins, ie. inducing an autolysis.

By induced autolysis is meant the production and activation of the intrinsic enzymes which break down the intracellular cell wall and proteins. Practical application of this method has to date been described only for simplifying the preparation of protein extracts from yeast fermentations. In the known process, only by induced autolysis is the required product formed.

The autolysis of microorganisms can be induced by stress factors.

Examples of possible stress factors for microorganisms are: nutrient deficiencies, temperature increases, oxygen deficiencies, pH changes and changes in the pressure or the osmolarity in the medium, but also addition of salts, surfactants or fatty acids to the medium or else irradiation with UV light or X-rays (cf. Acta Biotechnol. 5 (1985) 2, 129–136).

Examples of riboflavin-producing microorganisms which can be used are the producer strain of *Ashbya gossypii* and mutants thereof, the producer strain of *Eremothecium ashbyii* and mutants thereof, and microorganisms of the genera Candida, Torulopsis, Bacillus or Saccharomyces.

A particularly suitable stress factor which may be mentioned is a temperature increase with oxygen deficiency.

Thus, for example, the riboflavin-producing strains of *Ashbya gossypii* and mutants thereof can be lysed at from 35 to 55° C. within from 6 to 28 hours with almost complete exclusion of oxygen, ie. on heating without aeration (passing in air). The pH of the solution during this should be from 4 to 9.

The present invention therefore also relates to a process for increasing the riboflavin content in spray-dried discharges from riboflavin fermentations, which comprises inducing the production or activation of the enzymes which break down the cell wall and proteins in the case of the riboflavin-producing strains of *Ashbya gossypii* and mutants thereof by heating the fermentation solution, which contains the maximum yield of riboflavin, at a pH of from 4 to 9, preferably from 5 to 8, in particular from 6 to 7, with substantial exclusion of oxygen, ie. without aeration, for from 6 to 28 hours, preferably 14 to 24 hours, at from 35 to 55° C., preferably 40 to 49° C., in particular 40 to 48° C.

Although DE 29 20 592 which has been evaluated in detail above states that the riboflavin-containing fermentation broth is to be heated at from 50 to 65° C. for from 15 to 45 minutes and that this heating serves to lyse the cells and to reduce the viscosity of the broth, the effect in this case is quite different. This brief heat treatment merely disrupts the riboflavin-containing cells, allowing the cell contents to flow out. By contrast, the incubation of the fermentation solution at lower temperatures for several hours according to the invention brings about complete enzymatic breakdown of the solid constituents of the cells, ie. cells and cell walls are no longer detectable on examination of the solution under the microscope after autolysis (cf. Example 5a–d). Above about 55° C., and in some cases even above 50° C., the enzymes which break down the intra-cellular cell wall and proteins and are required for the autolysis according to the invention are irreversibly destroyed.

The starting material used according to the invention is a riboflavin-containing fermentation solution. The production of riboflavin by fermentation is known. In brief, this method entails a nutrient medium being sterilized and inoculated and incubated with a microorganism able to produce riboflavin, such as *Ashbya gossypii* or *Eremothecium ashbyii*. When the yield of riboflavin approaches or approximately reaches the maximum, the fermentation is stopped. After the autolysis of the fermentation solution which is induced according to the invention the riboflavin can be obtained in a conventional manner by centrifugation or decantation and subsequent spray-drying of the sediment.

It is possible by the process according to the invention to increase the riboflavin content in the spray-dried discharges from the fermenter generally by about 20% and in particular cases even by up to 45%.

The Examples which follow illustrate the invention.

EXAMPLE 1

After completion of a riboflavin fermentation using a strain of Ashbya gossypii, the resulting solution with a riboflavin content of >5 g/l was heated at the temperatures stated in Table 1 while stirring gently and without passing in air at a pH of about 6.5 for 17 hours (h). The resulting suspension was then examined under the microscope. The results are compiled in Table 1 which follows.

TABLE 1

| Example | Temperature | Visible under the microscope, besides riboflavin |
|---|---|---|
| 1a | 30° C. | many cells |
| 1b | 35° C. | many cells |
| 1c | 40° C. | few cells |
| 1d | 45° C. | no cells |
| 1e | 50° C. | no cells |
| 1f | 60° C. | many cells and their membranes |
| 1g | 70° C. | many cells and their membranes |

The results show that complete autolysis of the cells and cell walls contained in the fermentation solution is achieved by heating the discharge from the fermenter at 45° C. or 50° C. and pH 6.5, while stirring gently under quasi anaerobic conditions, for 17 hours.

EXAMPLE 2

After completion of a fermentation in which a riboflavin content of >5 g/l in the solution was achieved, the discharge from the fermenter was heated at 45° C. for 17 h, while stirring gently and without passing in air, at the pH values indicated in Table 2. After this, the solids in the solution were sedimented quantitatively in a laboratory centrifuge. The sediment was subsequently dried to constant weight, and the riboflavin content in the dry sediment was determined. For comparison (Example 2i), the untreated discharge was quantitatively sedimented, the sediment was dried, and the riboflavin content therein was determined.

TABLE 2

| Example | pH | Riboflavin content in the dry sediment [% by weight] |
|---|---|---|
| 2a | 4.0 | 20 |
| 2b | 5.0 | 25 |
| 2c | 6.0 | 32 |
| 2d | 7.0 | 42 |
| 2e | 8.0 | 34 |
| 2f | 9.0 | 28 |
| 2g | 10.0 | 20 |
| 2i (for comparison) | untreated fermentation solution | 20 |

EXAMPLE 3

After completion of a fermentation in a 2000 l fermenter, in which a riboflavin content of >5 g/l was obtained, the discharge from the fermenter was divided in two. One half was directly, ie. without autolysis, decanted and spray-dried, and the other half was incubated at 45° C. under quasi anaerobic conditions (gentle stirring without passing in air) at pH 6.8 for 24 h. The autolyzed fermentation solution was then decanted and spray-dried. The results are indicated in Table 3 below.

TABLE 3

| Example | Discharge from fermenter | Riboflavin content in spray-dried sediment [% by weight] |
|---|---|---|
| 3a | spray-dried without subsequent autolysis | 60 |
| 3b | spray-dried with subsequent autolysis | 90 |

EXAMPLE 4

After completion of a fermentation using a strain of Ashbya gossypii, the resulting solution with a riboflavin content of >5 g/l was incubated at 45° C. while stirring gently and without passing in air at pH 6.5. Samples were taken and investigated at intervals of from 2 to 4 h. For this, in each case 45 ml were centrifuged at 2200 revolutions per minute in a laboratory centrifuge for 5 minutes. The sediment was resuspended in the same volume of saline (0.9% strength aqueous NaCl solution) and centrifuged again as indicated above. The sediment was then lyophilized. The results are shown in Table 4.

TABLE 4

| Example | Duration of autolysis in hours [h] | Riboflavin content in the lyophilized sediment [% by weight] |
|---|---|---|
| 4a | 0 | 45 |
| 4b | 4 | 50 |
| 4c | 6 | 56 |
| 4d | 8 | 64 |
| 4e | 10 | 71 |
| 4f | 12 | 75 |
| 4g | 14 | 78 |
| 4h | 16 | 81 |
| 4i | 20 | 85 |
| 4j | 24 | 88 |
| 4k | 28 | 91 |

EXAMPLE 5

Comparison of the effect of heating the fermentation solution as disclosed in DE 29 20 592 (Examples 5a–5c) and the effect of the autolysis according to the invention.

After completion of a fermentation with Ashbya gossypii, the resulting solution with a riboflavin content of more than 5 g/l was divided up and incubated under the conditions shown in Table 5.

The samples were then centrifuged in a laboratory centrifuge, and the sediment was washed 2× with saline, resuspended and again centrifuged. The sediment was then lyophilized. The results are shown in Table 5.

TABLE 5

| Example | Incubation conditions Time | Temperature | Appearance under the microscope | Riboflavin content in the lyophilized sediment [% by weight] |
|---|---|---|---|---|
| 5a (comp.) | 45 min | 20° C. | many cells visible | 27 |
| 5b (comp.) | 45 min | 50° C. | many cells and cell walls visible | 29 |
| 5c (comp.) | 45 min | 65° C. | many cells and cell walls visible | 32 |
| 5d | 20 h | 45° C. | no cells or cell walls | 81 |

Heating at 50 to 65° C. for 45 minutes achieved lysis of the cells of *Ashbya gossypii*—as described in DE 29 20 592. By lysis is meant in this case disruption of the riboflavin-containing cells, allowing the cell contents to flow out. Thus, under the microscope the cell walls (cf. Example 5b and 5c) are still complete, and the biomass is contained in the lyophilized sediment. By contrast, under the autolysis conditions according to the invention (cf. Example 5d) there is complete enzymatic breakdown of the cells, ie. no cells or cell walls are visible in the fermentation solution under the microscope.

We claim:

1. A process for increasing the riboflavin content in spray-dried discharges from riboflavin fermentations, which comprises heating a fermentation solution of riboflavin-producing strains of *Ashbya gossypii* after completion of the riboflavin fermentation, at a temperature of from 40 to 50° C. and a pH of from 4 to 9, for from 6 to 28 hours, under gentle stirring without aeration, to induce lysis of cells by specific production or activation of the intracellular enzymes, until complete enzymatic breakdown of the cell wall and proteins occurs.

2. A process as claimed in claim 1, wherein the riboflavin-containing fermentation solution is heated at a pH of from 6 to 7 under quasi anaerobic conditions at from 40 to 49° C.

3. A process as claimed in claim 1, wherein the riboflavin-containing fermentation solution is heated at from 40 to 48° C.

* * * * *